US006656143B2

(12) United States Patent
Browd (10) Patent No.: US 6,656,143 B2
(45) Date of Patent: Dec. 2, 2003

(54) VACUUM FIXATION BAG FOR STABILIZING THE HEAD

(76) Inventor: Samuel Robert Browd, 360 S. 200 West, Suite D 506, Salt Lake City, UT (US) 84101

( * ) Notice: Subject to any disclaimer, the term of this patent is extended or adjusted under 35 U.S.C. 154(b) by 2 days.

(21) Appl. No.: 10/084,953

(22) Filed: Mar. 1, 2002

(65) Prior Publication Data

US 2002/0123706 A1 Sep. 5, 2002

Related U.S. Application Data

(60) Provisional application No. 60/272,701, filed on Mar. 1, 2001.

(51) Int. Cl.[7] .................................................. A61F 5/00
(52) U.S. Cl. .............................. 602/13; 602/17; 602/18
(58) Field of Search ............................... 602/13, 17–18, 602/5

(56) References Cited

U.S. PATENT DOCUMENTS

| | | | | |
|---|---|---|---|---|
| 3,397,688 A | * | 8/1968 | Gottfried | |
| 3,745,998 A | * | 7/1973 | Rose | |
| 4,885,811 A | * | 12/1989 | Hayes | |
| 5,454,781 A | * | 10/1995 | Chitwood | |
| 5,569,175 A | * | 10/1996 | Chitwood | |
| 6,079,056 A | * | 6/2000 | Fogelberg | |

* cited by examiner

Primary Examiner—Nicholas D. Lucchesi
Assistant Examiner—Lalita M. Hamilton (57) ABSTRACT

A vacuum fixation device to provide semi-rigid head fixation during medical imaging and medical procedures/operations of the face and head is disclosed. The invention addresses the problem of patient movement during medical/imaging procedures. The invention is a vacuum fixation bag that is designed to provide maximum surface area contact with the subject's head creating semi-rigid immobilization while allowing access to the face and cranial vault. The invention is comprised of an airtight flexible bag containing an effective amount of Styrofoam beads and a closable port providing semi-rigid fixation. The bag is especially configured to provide stabilization to the neck, the under surface of the mandible, the lateral head around the peri-auricular surfaces, and the forehead. The current invention is provided as a sterile, single use item that provides semi-rigid head fixation during medical imaging and medical procedures/operations of the face and head.

2 Claims, 9 Drawing Sheets

VACUUM FIXATION BAG FOR STABILIZING THE HEAD

This application claims benefit of U.S. provisional application No. 60/272,701 filed Mar. 1, 2001.

SPECIFICATION

This invention relates to a vacuum fixation bag and method of use thereof The. invention as described relates to a sterile vacuum fixation bag for use in stabilizing the head during medical and surgical procedures where the head must remain immobilized for prolonged periods of time. The device provides for semi-rigid fixation of the head within the setting of medical imaging studies including but not limited to computed tomography (CT), magnetic resonance imaging (MRI) studies, nuclear medicine studies and positron emission tomography (PET). The invention described is also suited for use during invasive procedures that require head fixation such as neurosurgical procedures, ophthalmologic procedures, cranio-facial surgery and other procedures involving the head and face that require head immobilization. The invention is designed for placement inside of standard imaging systems such as the head coil of an MRI scanner or the head platform of a CT scanner. The invention is suitable for head stabilization during cranio-facial procedures, neurosurgical procedures, opthomolgical procedures and any type of procedure requiring head immobilization by attachment to the operating or procedure table.

The current practice of medical imaging relies upon the acquisition of multiple images during the routine sequence of imaging a single subject. Often the acquisition of the serial images is compromised by patients moving their head during the imaging acquisition period. It is estimated that 30% of medical imaging, specifically, magnetic resonance imaging studies, need to be repeated due to head motion artifact. Additionally, newer imaging modalities rely on the reproducible location of sequential images to provide localizing information during studies such as functional MR imaging. The movement of subjects during such studies invalidates the data obtained and necessitates the reimaging of said individuals. The invention submitted addresses this problem by providing a non-invasive sterile device for semi-rigid head fixation during medical imaging procedures. The device is a single use, sterile vacuum fixation bag specifically designed to address the problem of patient movement during medical imaging. The invention is designed to fix the subject's head within the medical imaging device and provide semi-rigid fixation during the imaging procedure to reduce the need to repeat the imaging due to patient head movement.

The invention submitted also provides for semi rigid head fixation during medical procedures that require head fixation. The indications for usage would include any procedure where head immobilization is sought to either facilitate the procedure or protect the patient's head during the procedure. Current indications would include but not be limited to any type of craniofacial procedure including neurosurgical, ophthalmologic, otolaryngology, radiologic, dental or plastic surgery procedure where head stabilization is desired. The invention submitted provides for semi-rigid fixation by application to the subject's head and attachment of the device to the operating or procedure table. The invention is non-invasive and provides head fixation during procedures that require head immobilization.

The invention submitted is a single use, sterile vacuum fixation device for stabilization of the head during medical imaging or surgical procedures. The invention is a vacuum fixation device comprised of an airtight plastic bag which contains Styrofoam beads and a closable port for insertion and withdrawal of air. The unique configuration of the bag allows for semi rigid fixation of the head by providing contact along the under surface of the mandible, the lateral portion of the head bilaterally to contact the peri-auricular surfaces and a forehead portion configured for contacting the subject's forehead. The invention is also provided in a form that allows for access to the cranial vault for cranial procedures. Once fitted to the subject, air is evacuated from the bag via the closable port bringing the Styrofoam beads into close proximity to one another developing the semi rigid mold which provides the basis for the semi-rigid fixation. The device is then fixed to either the medical imaging device or the procedure table to secure the subjects head.

The vacuum fixation bag is made by methods well known in the art. The bag is made of a plastic material, such as any flexible plastic that is suitable for external use in a medical device. The foam beads can be made of any suitable multicellular expanded synthetic resinous material, such as Styrofoam. The closable stem is likewise made of flexible plastic which is melded to the bag to provide a passage for air into and out of the bag. The closable stem has a stopper at its distal end which can be opened to release air or inserted to prevent air from entering the system.

CROSS-REFERENCE TO RELATED APPLICATIONS

| U.S. Patents | | |
|---|---|---|
| 3,745,998 | July 1973 | Rose, et al. |
| 4,885,811 | December 1989 | Hayes, et al. |
| 6,079,056 | June 2000 | Fogelberg, et al. |
| 3,397,688 | December 1965 | Gottfried, et al. |
| 5,569,175 | October 1996 | Chitwood, et al. |
| 5,454,781 | October 1995 | Chitwood, et al. |

The application describes a head immobilization device that has a unique geometric configuration that addresses several issues unique to this patent application. Firstly, the device is configured to allow for semi-rigid fixation of the head using polymer beads contained within thin plastic sheeting. Rose, et al (U.S. Pat. No. 3,745,998) discuss vacuum immobilization and note "numerous evacuated envelopes have been proposed for use as rigidified immobilization devices" [Section 14, line 48]. Rose continues in their application to define more specifically the nature of the elastic materials and the filler; however in contrast to the current application, Rose only provides for very simple designs which are useful only during immobilization of a single extremity or of the body as a whole. The issues involved in immobilization of the head are not addressed in any fashion and the invention as described would not provide for adequate immobilization of the head. Adequate immobilization of the head requires specific points of contact to limit motion in flexion, extension, rotation, and lateral movement. Thus, while the general use of a vacuum immobilization device is presented by Rose, et al. the utility of this device for immobilization of the head is not feasible and not inferred in their application. The submitted invention provides a unique geometric design exclusively provided for immobilization of the head utilizing a well known technique which incorporates vacuum fixation.

Secondly, it is provided that Chitwood, et al. (U.S. Pat. No. 5,454,781) provides for a device used to provide cervical traction. The device only provides contact with the subject's neck area and a forehead strap is provided to further restrain the subject. The device provides for cervical traction/stretch and is not designed for immobilization. This device, as described, fails to provide fixation of the head in such a fashion as to prevent movement. The subject would be able to move their head in several directions since the device only provides fixation about the neck and forehead. Lateral movement of the head is not addressed nor is flexion/extension. Chitwood, et al. provides a continuation of U.S. Pat. No. 5,441,479 in their U.S. Pat. No. 5,569,175. U.S. Pat. No. 5,569,175 was also provided as evidence of prior art. Chitwood, et al again describe a continuation of their earlier work now providing a platform for attaching the cervical traction device. Again, this invention in not designed for head immobilization and to the contrary, is designed for "rotation of the platform about any one of or all of an x-axis, a y-axis, and a z-axis" [Section 2, line 10–11]. Chitwood, et al. fail to describe a device that is intended for head immobilization and to the contrary describe a device that promotes movement of the head while producing traction of the neck. The current invention submitted (Ser. No. 10/084,953) does not produce traction of the neck since this effect would be deleterious in many patient/subject populations for which the device is intended. Cervical traction is utilized in very specific medical conditions and its general application can be unsafe; additionally, is not the standard of care to use cervical traction for head immobilization.

Three additional patents are provided as references. Gottfried, et al., U.S. Pat. No. 3,397,688 provides for a pneumatic head and neck immobilizer. The device discussed by Gottfried provides immobilization by inflating a device around a subject's head and securing the device under the armpits. The device fails to provide a similar utility as the submitted invention for several reasons. First, the device by Gottfried does not allow access to the head or the auditory canal a feature which is critical for use during medical procedures. Secondly, the device fails to adequately define the degree of immobilization as no portion of the device resides under the chin of the subject; thus flexion and lateral movements are possible with this system. Thirdly, the invention by Gottfried, et al. is likely to produce some degree of downward axial traction on the cervical spine as it is designed, a feature which is not desirable in the context of patient care. Lastly, the device is too large and cumbersome to fit within modern imaging devices. Additionally, the device functions by inflation and could damage delicate imaging equipment such as an MRI head coil. It is therefore provided that the invention of Gottfried, et al. has no relationship to the proposed invention.

Fogelberg et al., U.S. Pat. No. 6,079,056, provide a device for air cushioning during sports. The device has no bearing on the current invention submission. Fogelberg's device is for prevention of sporting injuries and would not provide any support of the head nor would the device reduce head movement in any fashion. The construct of this invention is to go around the head and provide impact protection to the shoulders, clavicles and scapular areas. Additionally, the materials of construction are different than the submitted invention and would not be feasible for use in the current application.

Hayes, et al. U.S. Pat. No. 4,885,811, provides a device for protection of bodies during transport. The invention of Hayes discusses a vacuum fixation mold which provides for immobilization of the entire body between two sheets. The device does not provide for head immobilization as such and would not allow access to the face, auditory canals, or cranial vault. The invention of Hayes does not provide specific design characteristics which provide for head immobilization, nor does the device size allow for its use in medical imaging equipment or during other medical procedures. Thus, while the general use of a vacuum immobilization device is presented by Hayes, et al. the utility of this device for immobilization of the head is not feasible and not inferred in their application. The submitted invention provides a unique geometric design exclusively provided for immobilization of the head utilizing a well known technique which incorporates vacuum fixation.

It is therefore proposed that the current application is distinctly different from the other applications provided as proof of the current art. The invention "Vacuum fixation bag for stabilizing the head" is a unique concept specifically designed to address the unique problems of head fixation. While the utilization of vacuum fixation has been used by many others, the specific geometric design and medical applications of this invention have not been proposed or inferred in other patents.

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISK APPENDIX

Not applicable

BACKGROUND OF INVENTION

The invention relates to a vacuum fixation device and method of use thereof with applications for, but not limited to, head stabilization during medical imaging and surgical procedures. The first application of the invention is in the field of medical imaging. Newer imaging techniques such as magnetic resonance imaging, computed tomography, and nuclear imaging studies are obtained by acquiring repeated images of the head over time. Some of these procedures can last for long periods of time and require of subjects long periods of movement restriction. Under current imaging conditions, it is difficult for even the most compliant subjects to remain motionless for extended periods of time. Movement that occurs during medical imaging causes multiple problems including degradation of imaging quality, difficulty with image alignment and most importantly these limitations often necessitate repetition of imaging cycles to obtain artifact free imaging. More sophisticated imaging techniques such as functional magnetic resonance imaging requires multiple images, obtained over long periods, to be overlaid on one another to evaluate signal characteristics within single image voxels over time. Head movement during such procedures make temporal analysis of regions of interest difficult if not fully unreliable. The invention submitted allows for movement restriction during these types of medical imaging procedures by providing semi-rigid head fixation within the imaging device.

It is difficult for motivated subjects to remain motionless during these imaging procedures but it is even more difficult to image noncompliant subjects. Specific examples would include children and subjects with learning disabilities or comprehension deficits. These subjects often present a marked challenge to acquiring adequate, motion-free images due to their inability to remain motionless during imaging. These subjects often must be sedated with medication prior to undergoing imaging and because of this necessity these subjects endure the risks associated with anesthesia and sedation. The invention submitted is suitable for use during imaging of non-compliant subjects and will reduce the necessity to sedate these subjects during medical imaging.

Many devices have been developed to address the issue of head movement during medical imaging. These devices have included solid bite bars and plastic molds of the subject's face. These devices have provided poor results and are not suitable for the majority of subjects who undergo medical imaging. One specific example relates to the use of these devices in patients with seizure disorders or in subjects who have any risk of developing seizure activity such as head trauma patients. Rigid fixation within the scanning environment is not safe because of concerns regarding trauma during a seizure directly from the device or the compromise of a subject's airway during a seizure event. The current invention provides a safe method to restrain the subject's head without compromising safety or airway access. The current invention is semi-rigid and will deform if sufficient force is applied as when a seizure event occurs. Additionally, the current invention provides head restraint without covering the face or airway thus providing freedom from airway obstruction and access to the subject's face if needed in a medical emergency.

The current state of head stabilization in the majority of imaging centers worldwide is to use strips of foam padding and surgical tape to secure the subject's head within the imaging device. This procedure is time consuming, provides little head stabilization, and is non-hygienic. The current invention provides for efficient, hygienic, comfortable head stabilization without the risks associated with rigid head fixation.

The economic impact of being able to image subjects without head movement is an important aspect to the utility of this invention. Routine medical imaging is a multi-billion dollar segment of the health services industry and a major portion of the gross domestic product of the United States. Billions of dollars from private, corporate, insurance, and governmental agencies are spent each year on medical imaging. These costs could be reduced if medical imaging procedures were obtained on the initial attempt without the need to repeat a portion of the procedure. If fewer studies needed to be repeated, then the productivity of imaging centers would increase and patient access to these resources would increase as well.

A second indication of the current invention is to provide head stabilization during medical procedures. Many fields of medicine provide care for the upper portion of the body including the regions of the head and face. Many invasive and non-invasive procedures performed on the head and face require that the head and neck be immobilized during the time the procedure or surgery takes place. Inclusive in this arena is the application of intra-operative imaging techniques whether frameless or frame dependent technology and other types of imaging studies including but not limited to cerebral angiography. It is established that head fixation is necessary in most neurosurgical and craniofacial procedures. This fixation is currently obtained using rigid, invasive head fixation, for example using a Mayfield head holder, which uses skull pins to clamp the subject's head rigidly to a frame which is secondarily attached to the operative table. Many neurosurgical and craniofacial procedures do not require such rigid fixation and semi-rigid fixation would be more appropriate while still providing for patient safety and surgeon comfort and access. Examples include but would not be limited to brain biopsies, awake craniotomy procedures, smaller neurosurgical cases such as ventricular peritoneal shunt placements or revisions and a variety of craniofacial and neurosurgical procedures performed on children. Many traumatic injuries also can be managed with semi rigid vs. rigid fixation. Additional uses would include but not be limited to functional neurosurgical procedures where stereotactic localization is performed to obtain biopsy coordinates or localization for placement of neuro-implants.

The current invention will provide stabilization in four critical locations including the forehead, ears, chin and jaw, yet the entire face remains exposed as to provide access for anesthesia and surgical operations in that area. The cranial vault is likewise exposed and available for any variety of cranial procedures. While the device allows for semi-rigid fixation and access to the face and cranial vault, the invention eliminates several risks associated with rigid fixation including skull fractures, extra and intracranial bleeding from skull pin application, and the risk of superficial and deep infections that result from skull pin placement using devices such as the Mayfield head holder.

The invention is provided as a single use, sterile item and would alleviate the necessity to sterilize the item prior to usage. This promotes rapid operative and procedure room turn over making the medical institution more productive and cost efficient.

In view of the foregoing, it will be appreciated that providing a vacuum fixation device for use in medical imaging and medical procedures/surgery that is hygienic, inexpensive, comfortable, and immobilizes the head at critical points of contact including the forehead, ears, chin, and jaw while providing access to the face and cranial vault would be a significant advancement in the art.

BRIEF SUMMARY OF THE INVENTION

The current invention submitted is a vacuum fixation device designed to provide semi-rigid head fixation during medical imaging and medical procedures/operations of the face and head. The invention is a vacuum fixation bag that is designed to provide contact with the subject's head creating semi-rigid immobilization. The invention is comprised of an airtight flexible bag containing an effective amount of Styrofoam beads and a closable port configured for passage of air into and out of the bag such that when air is evacuated from the bag, the beads conform to the head providing semi-rigid fixation. The bag is especially configured to provide stabilization to the neck, the under surface of the mandible, the lateral head around the peri-auricular surfaces, and the forehead. The configuration of the invention provides full access to the subject's face and cranial vault while providing access to the auditory canals, a feature which is desired during medical imaging studies where communication with the subject is desired or during surgery where the patient is awake.

The current invention is provided as a sterile, single use item that provides semi-rigid head fixation in an inexpensive, comfortable format during medical imaging procedures and during medical procedures/surgery involving the face and/or head.

An invention is detailed for stabilizing a subject's head during medical imaging procedures and during medical procedures/surgery involving the face and/or head comprising:

a) a vacuum fixation device comprised of an airtight flexible bag containing an effective amount of beads, the bag comprising a neck-ring portion configured for mandible fixation, a lateral head portion configured for contacting peri-auricular surfaces of the subject's head, a forehead portion configured for contacting the subject's forehead, and a closable port for passage of air into and out of the bag;

b) stabilizing the inferior aspect of the mandible with the neck ring portion, stabilizing and fixing the subject's periauricular cranium with the lateral head portion, and the subjects' forehead with the forehead portion of the vacuum bag; and c) evacuating air from the vacuum fixation bag such that the vacuum fixation bag and beads conform to the subject's head, thereby forming a semi-rigid cast whereby the head can be fixed either within the medical imaging device or to the operating/procedure table during procedures involving the face or head.

d) The vacuum fixation bag fixes the head at four critical axes of potential movement (mandible and forehead [out-of-plane movement], and bilateral peri-auricular surfaces [in-plane movement]).

e) The configuration of the device provides semi-rigid fixation but allows access to the entire face and cranial vault f) The device is semi-rigid but deformable under adequate stress providing a safe mechanism to restrain non-compliant subjects such as children or those with mental capacity that limits their ability to comply during imaging procedures/medical procedures.

BRIEF DESCRIPTION OF THE SEVERAL VIEWS OF THE DRAWINGS

FIG. 6 shows a perspective view of the vacuum fixation bag diagrammed in FIG. 1 with a subject in phantom and air withdrawn from the bag, thus fixing the subject's head. FIG. 6 shows the device deployed within a generic cervical/cranial cradle which attaches to the imaging platform table, such an example might represent the use of the vacuum fixation bag during routine computed tomography imaging.

DETAILED DESCRIPTION

Before the present vacuum fixation bag and method of use thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a", "an", and "the" include plural references unless the context clearly dictates otherwise.

In describing and claiming the present invention, the following terminology will be used in accordance with the definitions set out below.

As used herein, "comprising", "including", "containing", "characterized by", and grammatical equivalents thereof are inclusive or open-ended terms that do not exclude additional, unrecited elements or method steps. "Comprising" is to be interpreted as including the more restrictive terms "consisting of" and "consisting essentially of".

The current invention submitted is a vacuum fixation device designed to provide semi-rigid head fixation during medical imaging and medical procedures/operations of the face and head. The invention is designed to address the problem of patient movement during medical imaging and medical procedures/operations of the face and head. The invention is a vacuum fixation bag that is designed to provide maximum surface area contact with the subject's head creating semi-rigid immobilization while allowing access to the face and cranial vault. The invention is comprised of an airtight flexible bag containing an effective amount of Styrofoam beads and a closable port configured for passage of air into and out of the bag such that when air is evacuated from the bag, the beads conform to the head providing semi-rigid fixation. The bag is especially configured to provide stabilization to the neck, the under surface of the mandible, the lateral head around the peri-auricular surfaces, and the forehead. The unique configuration of the invention provides full access to the subject's face and cranial vault while providing access to the auditory canals, a feature which is desired during medical imaging studies where communication with the subject is desired or during surgery where the patient is awake.

The current invention is provided as a sterile, single use item that provides semi-rigid head fixation in an inexpensive, comfortable format during medical imaging procedures and during medical procedures/surgery involving the face and/or head.

The first five figures demonstrate the use of the invention during routine medical imaging, with specific illustration of its use during routine magnetic resonance imaging. The general principles of use during routine medical imaging would transcend other imaging modalities including all forms of magnetic resonance imaging, computed tomography, nuclear medicine studies among other imaging modalities.

Figure 1:
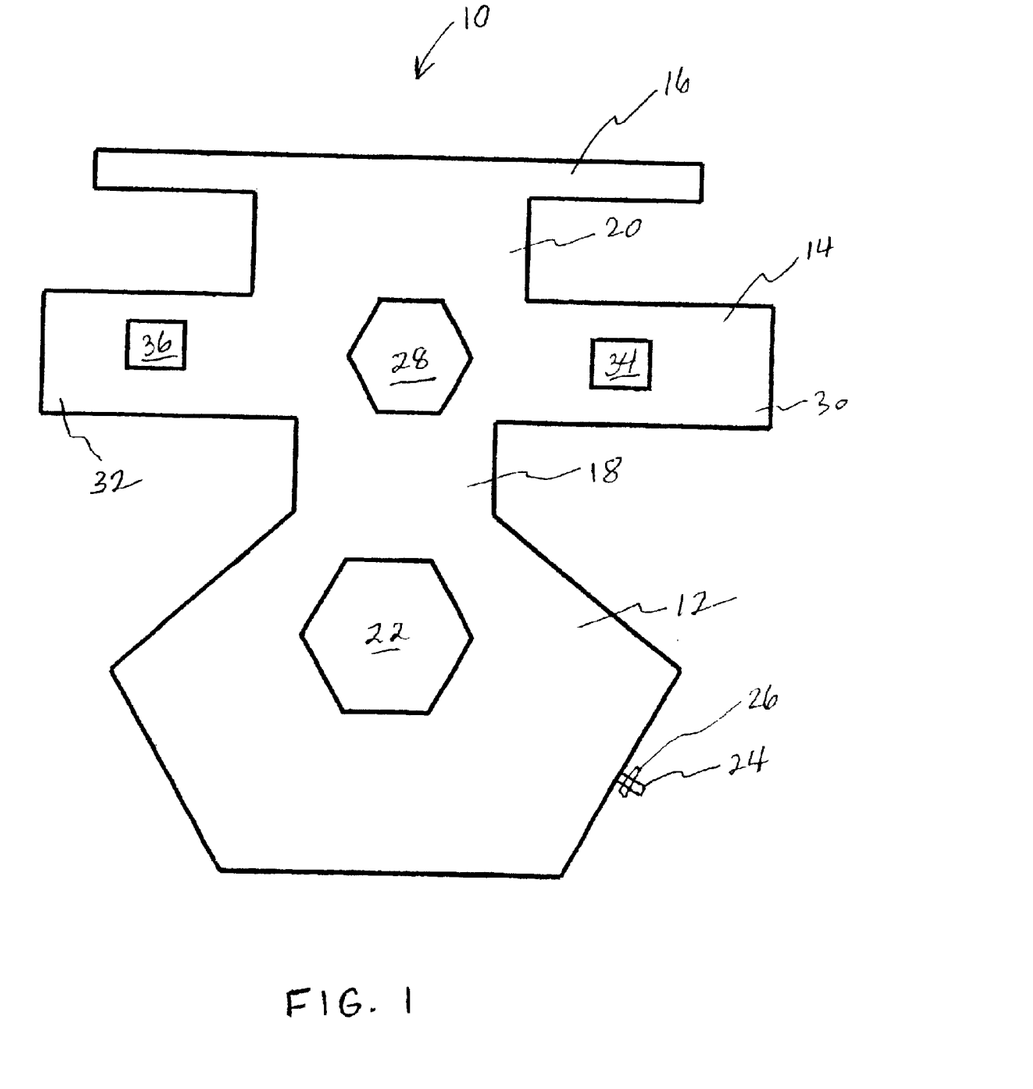
FIG. 1 shows a schematic diagram of an illustrative vacuum fixation bag according to the present invention.

FIG. 1 shows a schematic diagram of an illustrative vacuum fixation bag 10 according to the present invention.

The vacuum fixation bag comprises a neck-ring portion 12 for stabilizing the subject's mandible and posterior cervical spine; a lateral-head portion 14 for cradling the back of the head and stabilizing the lateral head; and a forehead portion 16 for stabilizing the forehead. These three portions are contiguous with each other, the neck ring and lateral-head portions being joined by a dorsal neck portion 18 that contacts the back of the subject's neck, and the lateral-head and forehead portions being joined by a top portion 20 that contacts the top of the subject's head.

Figure 3:
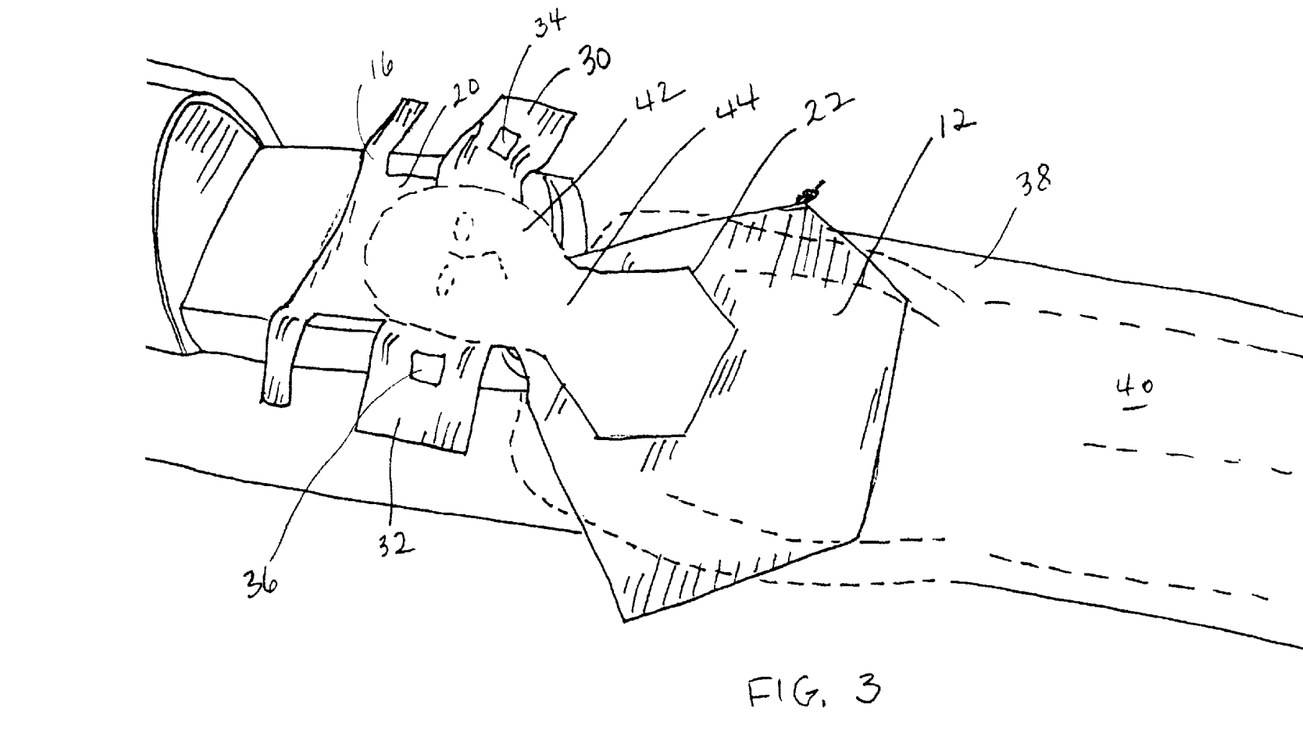
FIG. 3 shows a perspective view of the vacuum fixation bag diagrammed in FIG. 1 with a subject in phantom.
Figure 4:
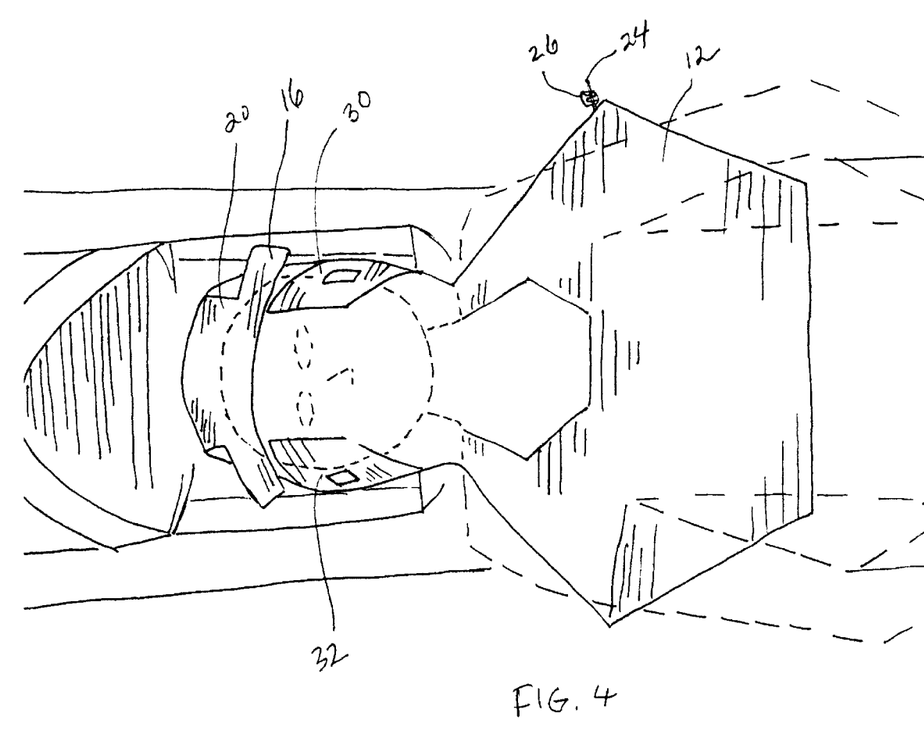
FIG. 4 shows a perspective view of the vacuum fixation bag diagrammed in FIG. 1 with a subject in phantom and the vacuum fixation bag positioned around the subject's head.

The neck ring portion 12 comprises a cut-out 22 through which the subject's head is initially inserted such that the neck-ring portion forms a ring around the subject's neck (FIGS. 3 and 4). Prior to evacuating the vacuum fixation bag, the neck-ring portion is mobilized to the undersurface of the subject's mandible. The neck-ring portion 12 also preferably comprises a port 24 through which suction is applied to evacuate the air from the inside of the bag. The port 24 is closable by means of a valve or clamp 26 such that suction does not need to be continuously applied. After the air is evacuated, the port is closed with the valve or clamp, thus maintaining a negative pressure inside the bag.

The lateral-head portion 14 comprises a central cut-out 28 on which the subject rests the back of his or her head. The lateral-head portion also comprises two lateral wings 30 and 32, which are placed alongside the lateral head area to provide support to peri-auricular surfaces. Each lateral wing comprises a cut-out 34 and 36 designed to be placed over the ears of the subject (FIG. 4) such that the ears are not covered and there is access to the subject's ears for use of auditory equipment or facilitation of routine communications with the subject during medical imaging procedures.

Figure 2:
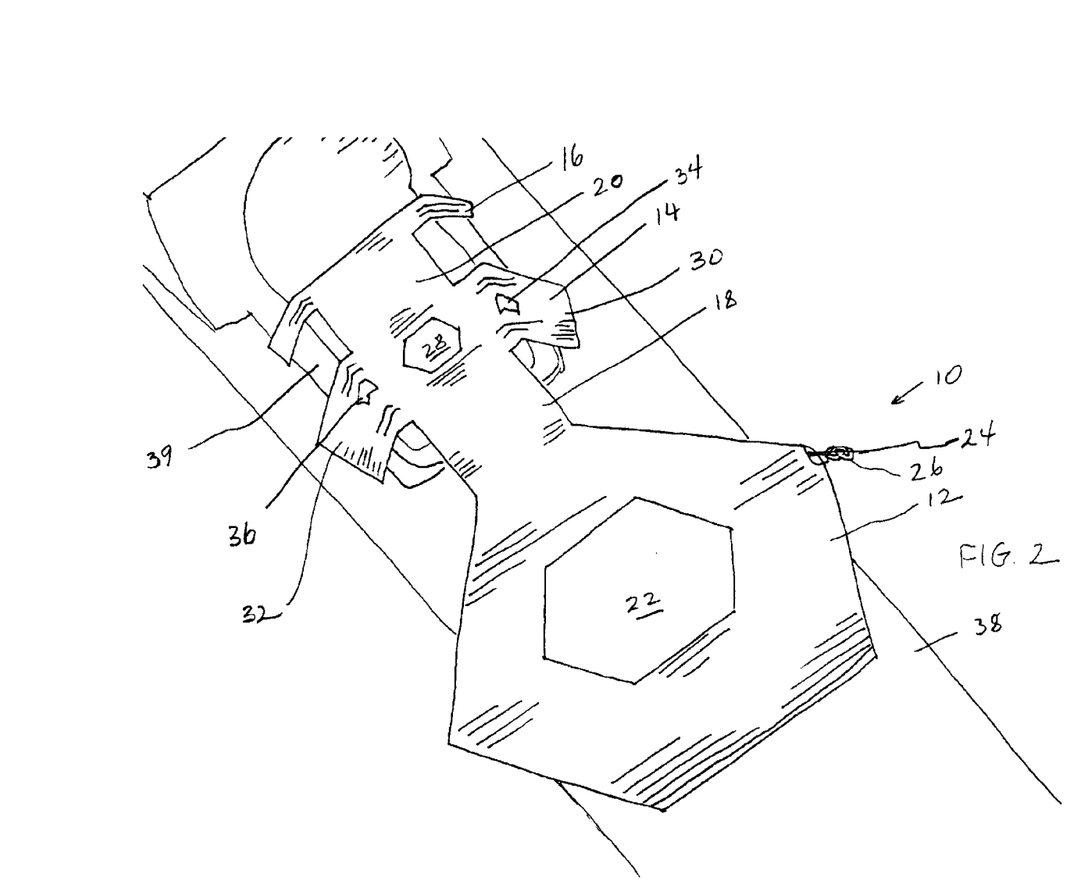
FIG. 2 shows a perspective view of the vacuum fixation bag diagrammed in FIG. 1.

FIG. 2 shows a perspective view of the vacuum fixation bag 10 spread out on the table portion 38 and head coil 39 of the MRI machine.

FIG. 3 shows a subject 40 lying on the table. The head 42 and neck 44 are extended through the cut-out 22 of the neck-ring portion 12 of the vacuum fixation bag such that the neck-ring portion 12 encircles the neck. The back of the head of the subject is rested on the lateral-head portion, centered over the central cut-out 28 (FIGS. 1 and 2).

FIG. 4 shows that the lateral wings 30 and 32 are placed alongside the lateral side of the subject's head, with the ear cut-outs 34 and 36 over the ears of the subject. The forehead portion 16 of the bag is brought over the top of the subject's head such that the top 20 contacts the top of the head and the forehead portion 16 contacts the forehead. Prior to evacuation, the neck ring portion 12 is mobilized to the undersurface of the subject's mandible. With the bag arranged as described, the air in the bag is removed by applying suction to the port, then the valve or clamp 26 is used to close the port to maintain the negative pressure within the bag. Suction is applied by any conventional means known in the art, such as a vacuum pump. When the air is evacuated from the bag, the bag and the beads contained therein conform to the head, creating a comfortable, form-fitted mold of the head. This form-fitted mold comprises a semi-rigid cast of the head.

Figure 5:
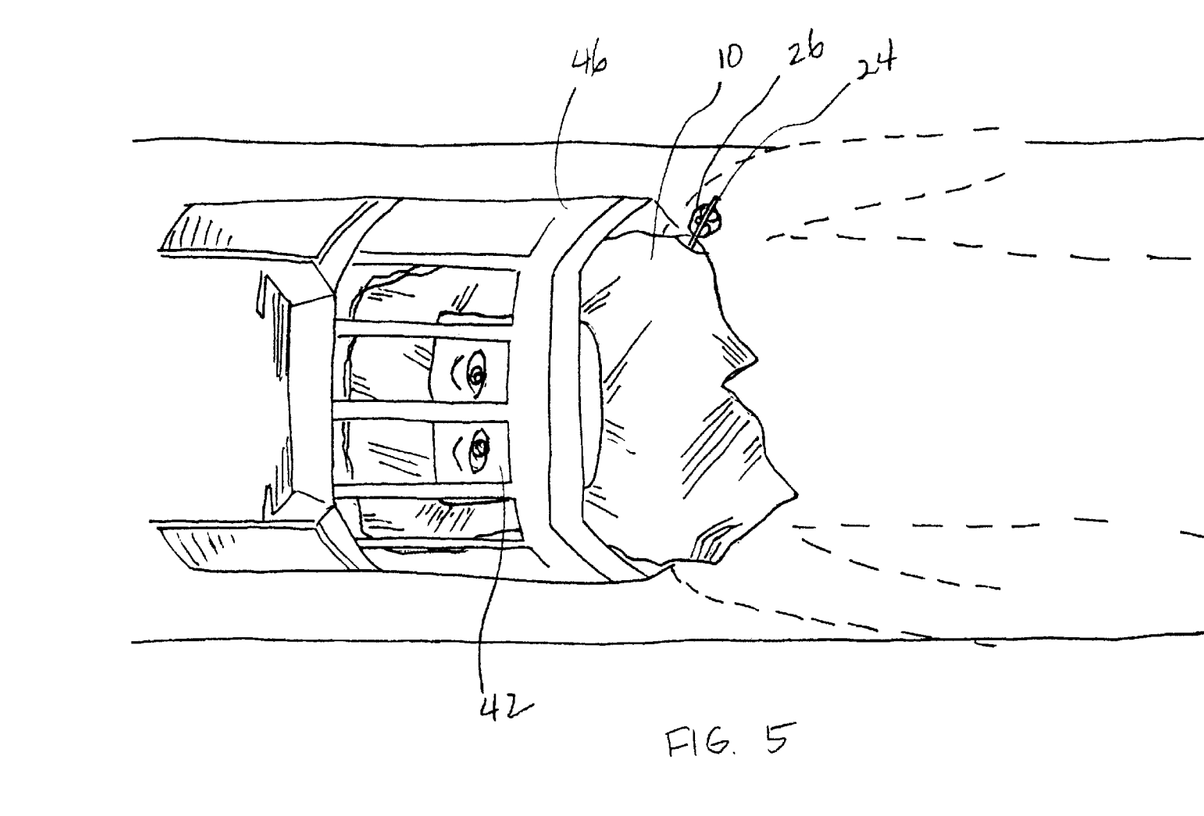
FIG. 5 shows a perspective view of the vacuum fixation bag diagrammed in FIG. 1 with a subject in phantom and air withdrawn from the bag, thus fixing the subject's head within the MRI head coil as a representative example of its use in medical imaging.

FIG. 5 shows the vacuum fixation bag 10 holding the subject's head in a fixed or stabilized position with the magnetic resonance head frame. The form-fitted mold is compact enough that the head coil 46 of the MRI machine fits/slides over the subject's immobilized head, yet the visual field and respiration of the subject are not compromised. The head is held in an immobile position, however by suitable force the subject could deform the bag and free themselves from the vacuum fixation bag, which is an important feature when subjects with epilepsy and other convulsive disorders are studied. The vacuum fixation bag is easily removed by allowing air into the bag, which relaxes the form-fitted mold by permitting beads to move inside the bag.

In situations where the vacuum fixation bag is not tight between the head coil, synthetic foam strips can be used to secure the vacuum bag within the head holder thus providing outward resistance to deformation of the vacuum fixation bag. This procedure is standard practice in the majority of imaging centers.

Figure 6:
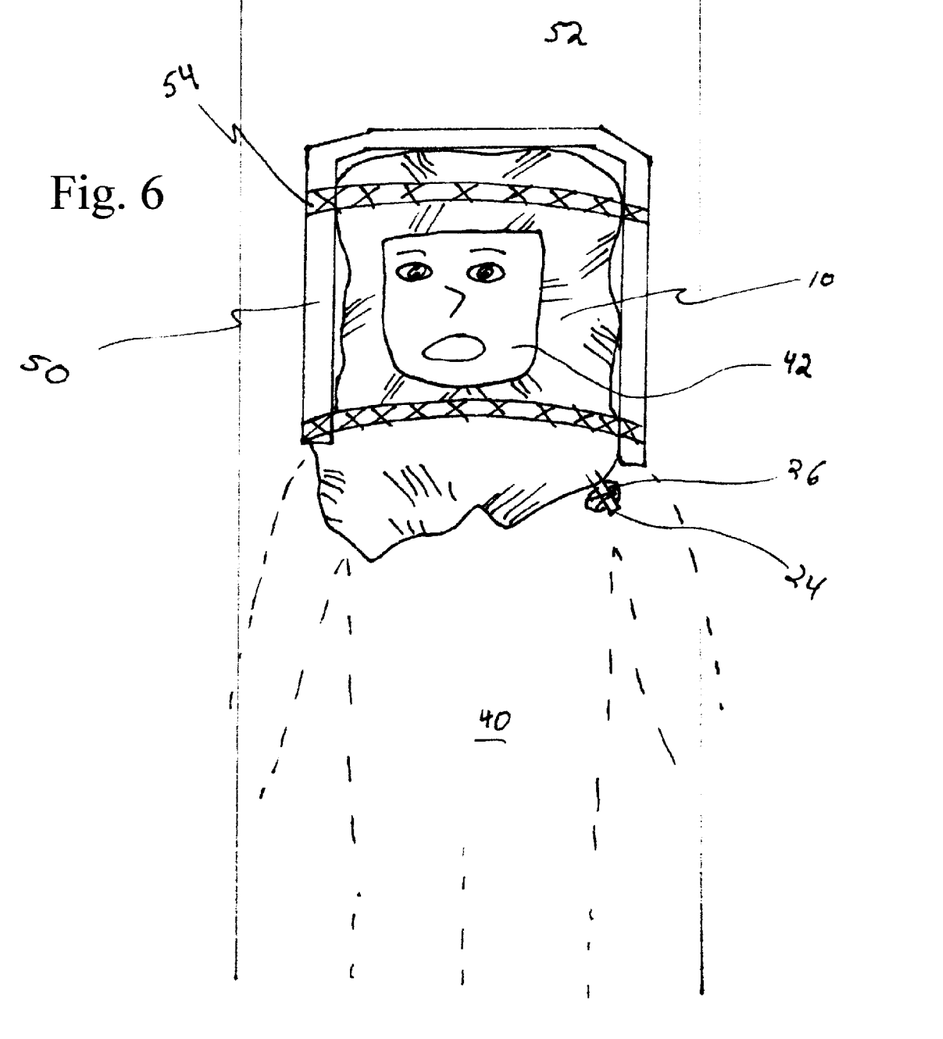

Adaptation of the vacuum fixation bag can be made for any imaging system by incorporating a variety of devices that attach to the imaging platform and accept the patient's head as it is enclosed by the vacuum fixation bag. FIG. 6 demonstrates the vacuum fixation bag being applied during routine computer tomography imaging. The cervical/cranial cradle 50 is attached to the imaging platform 52 in a standard fashion. The subject 40 is placed supine on the imaging platform and the vacuum fixation bag 10 is placed about the subject's head in the described fashion. The subject's head is placed into the cradle with the vacuum fixation device in place. Retention straps 54 are situated over the forehead portion and the cervical portion of the vacuum fixation bag and provide external resistance to vacuum bag deformation. A variety of solutions exist in current practice to accommodate the vacuum fixation bag and provide external resistance to prevent deformation of the vacuum fixation bag as it is affixed to various medical imaging devices.

Figure 7:
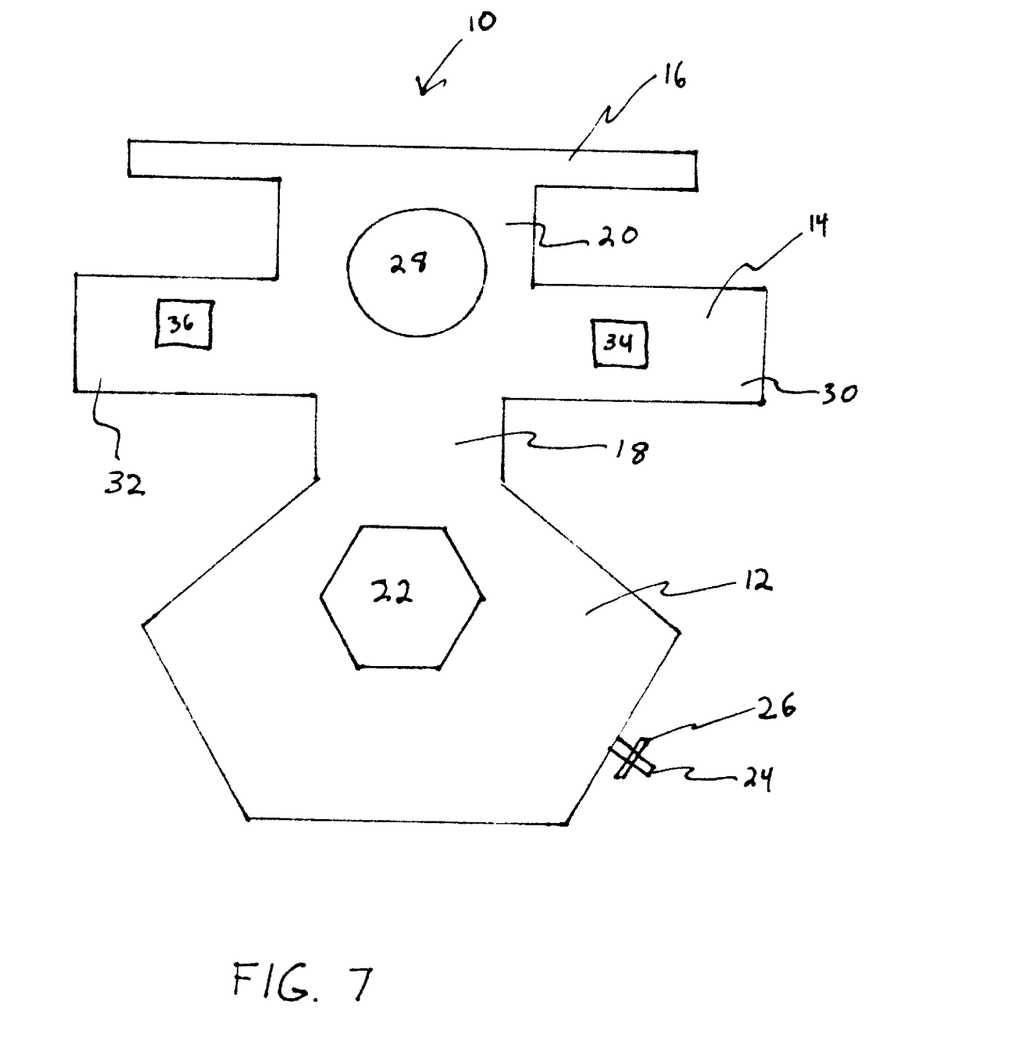
FIG. 7 shows a schematic diagram of an illustrative vacuum fixation bag according to the present invention adapted for use during medical procedures or surgery.

Application of the vacuum fixation bag during medical procedures or surgery to the craniofacial region require minor adaptation to the vacuum fixation bag. FIG. 7 illustrates the minor change made in the vacuum fixation bag for use during medical procedures or surgical intervention in the craniofacial region. The cut-out region for the posterior region of the skull 28 is slightly enlarged and circular to facilitate access to the cranial vault. The cut-out region 28 is also moved somewhat superiorly to occupy a portion of area 20 in the vacuum fixation bag design. The remainder of the invention remains unchanged. The minor adaptation described provides improved visualization of the cranial vault while retaining the critical points of contact around the forehead, lateral peri-auricular areas and inferiorly under the mandible. The adaptation for procedural/surgical use is created to allow the maximum exposure of the cranial vault while maintaining maximal surface area contact with the four critical points of fixation. Importantly, the entire face area remains open, an important feature during procedures and surgery where airway protection and access for resuscitation/anesthesiology is critical. The area of the face that is exposed could also be accessed during procedures that involve, but are not limited to, the eyes, face, sinuses, maxillofacial surgery and other craniofacial surgical and reconstructive procedures.

Figure 8:
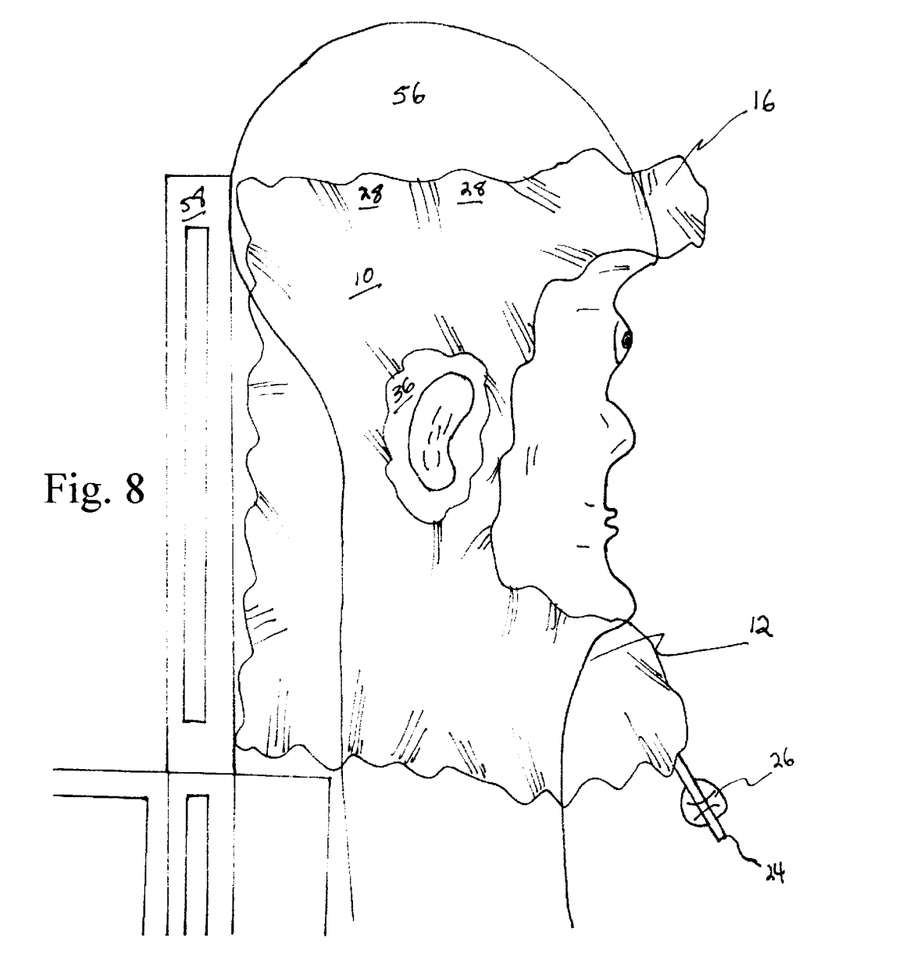
FIG. 8 shows a side view of the vacuum fixation bag illustrated in FIG. 7 deployed about the subject's head while they lie on a surgical table.

FIG. 8 is a side view demonstrating the vacuum fixation bag in use during an operative procedure (operating room table 58) where the cranial vault 56 would need to be accessed such as during a neurosurgical procedure. The vacuum fixation bag 10 is applied in the described fashion with the cut-out 28 situated over the cranial vault to allow for maximum exposure of this area and the neck ring portion 12 pressed underneath the mandible. Air is evacuated in the standard fashion through the port 24 and the clamp 26 is applied once all the air has been evacuated properly.

Figure 9:
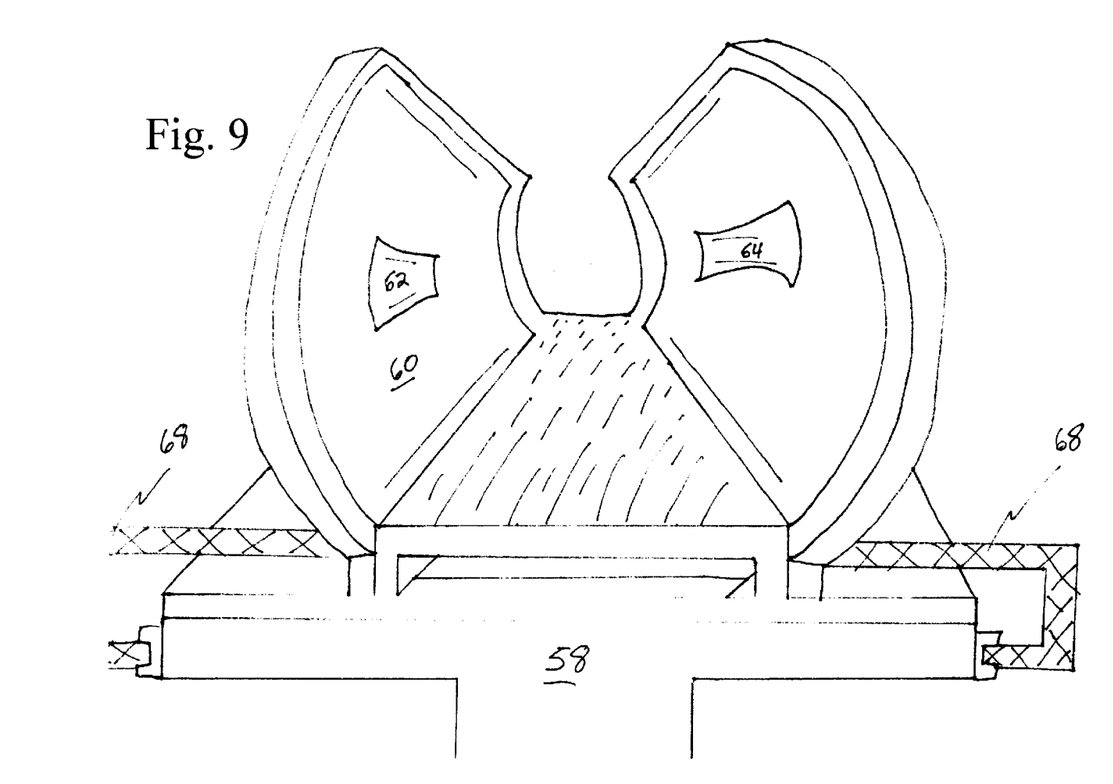
FIG. 9 shows head-on view of a representative generic cervical/cranial cradle which would be used to secure the vacuum bag to either an imaging platform table or a medical procedure/surgical table.

FIG. 9 illustrates a head-on view of a representative generic cervical/cranial cradle 60 which would be used to secure the vacuum bag to either an imaging platform table or a medical procedure/surgical table 58. The view is a head-on projection of cervical/cranial cradle 60 which is attached in a standard fashion to the operating room table 58 with a variety of clamping devices 68. The subject is placed supine on the imaging platform or procedure/surgical table and the vacuum fixation bag is placed about the subject's head in the described fashion. The subject's head is placed into the cradle 60 with the vacuum fixation device in place. The cut-out regions around the ears are centered over the lateral windows 62 and 64 cut into the walls of the cradle. Retention straps (not shown) would be situated over the forehead portion and the cervical portion of the vacuum fixation bag and provide external resistance to vacuum bag deformation. A variety of solutions exist in current practice to accommodate the vacuum fixation bag and provide external resistance to prevent deformation of the vacuum fixation bag as it is affixed to various medical imaging devices and procedural/surgical tables. FIG. 9 is an illustrative example of such an ancillary device.

The vacuum fixation bag is made by methods well known in the art. The bag is made of a plastic material, such as any flexible plastic that is suitable for external use in a medical device. The foam beads can be of any suitable multicellular expanded synthetic resinous material, such as Styrofoam. The port and valve/clamp are likewise made of plastic material well known in the art. The process for molding the port are well known in the art. The vacuum fixation bag is made by cutting the flexible plastic material into the shape described. Two sections are cut per bag. The port is then molded onto the noted section of the vacuum fixation bag to form an airtight connection in a fashion well known in the art. The edges of the sheets are then sealed in a fashion well known to the art. Prior to closing the last edge, the foam beads are placed into the interior of the bag in an amount appropriate for the application and the final edge is sealed. The device is then sent for terminal sterilization using methods well known in the art.

What is claimed is:

1. A vacuum fixation device configured to provide semi-rigid fixation during medical imaging and medical procedures/operations and configured to provide stabilization to the head and neck, the under surface of the mandible, the lateral head around the peri-auricular surfaces, and the forehead thereby allowing full access to the subject's face and cranial vault while providing access to the auditory canals comprising:

a sterile, single use bag configured to provide maximum surface area contact with the subject's head creating semi-rigid immobilization while allowing access to the face and cranial vault;

wherein the sterile, single-use bag is a polygonal-shaped device having upper and lower ends and an opening, whereby the opening is configured to fit around the neck of a patient;

wherein the sterile, single-use bag is airtight and flexible and contains an effective amount of filler material;

a closable port formed contiguous with the sterile, single-use bag for allowing passage of air into and out of the bag; and suction means adapted to be connected to the closable port, such that when air is evacuated from the bag, the filler material conforms to the head providing semi-rigid fixation.

2. The vacuum fixation device of claim 1, wherein said vacuum fixation device is configured to be secured to a fixed, rigid structure.

* * * * *